United States Patent [19]

Terada et al.

[11] 4,378,691
[45] Apr. 5, 1983

[54] MULTI-FUNCTIONAL SENSOR

[75] Inventors: Jiro Terada; Tsuneharu Nitta, both of Katano, Japan

[73] Assignee: Matsushita Electric Industrial Co., Ltd., Osaka, Japan

[21] Appl. No.: 229,181

[22] Filed: Jan. 28, 1981

[30] Foreign Application Priority Data

Apr. 2, 1980 [JP]  Japan ................................. 55-12889
Apr. 2, 1980 [JP]  Japan ................................. 55-12890

[51] Int. Cl.³ ..................... G01N 27/12; G01N 31/06
[52] U.S. Cl. ..................................... 73/27 R; 73/29; 338/34; 338/35; 422/98
[58] Field of Search ............... 73/23, 27 R, 29; 422/90, 98; 324/71 SN; 338/22 SD, 34, 35; 340/634

[56] References Cited

U.S. PATENT DOCUMENTS

| | | | |
|---|---|---|---|
| 3,906,473 | 9/1975 | Le Vine | 422/98 |
| 4,012,692 | 3/1977 | Eicker | 422/98 |
| 4,067,655 | 1/1977 | Miyaguchi | 338/34 |
| 4,086,556 | 4/1978 | Nitta et al. | 338/35 |
| 4,244,918 | 1/1981 | Yasuda et al. | 422/98 |

FOREIGN PATENT DOCUMENTS 54-123099  9/1979  Japan ..................................... 338/34

*Primary Examiner*—Howard A. Birmiel
*Attorney, Agent, or Firm*—Burgess, Ryan and Wayne

[57] ABSTRACT

A multi-functional sensor capable of sensing the humidity and the concentration of reducing gases in the surrounding atmosphere with a single sensing element of p-type metal-oxide ceramic semiconductor is provided. When the ambient temperature is lower than 150° C., the sensor can detect humidity in terms of variations in ion conduction due to the physical absorption of water by the sensing element, but when the ambient temperature or the temperature of the sensing element is at temperatures between 200° and 600° C., the sensor can detect the presence or concentration of reducing gases in the surrounding atmosphere in terms of variations in electron conduction due to the chemical absorption of gases by the sensing element.

6 Claims, 6 Drawing Figures

MULTI-FUNCTIONAL SENSOR

BACKGROUND OF THE INVENTION

The present invention relates to a multi-functional sensor with a single sensing element which corresponds to the amounts of water vapor and other gases in the surrounding atmosphere with a higher degree of sensitivity and which can detect the humidity and the concentration of reducing gases in the surrounding atmosphere in terms of variations in electrical resistance across the sensing element.

So far special sensors have been used to sense or detect the humidity and the presence of gases in the surrounding atmosphere. For instance, humidity sensing elements have been used exclusively in conjunction with humidity measuring instruments and humidity controlling systems and gas sensing elements have been used exclusively in conjunction with instruments for gas concentration and gas leakage alarming systems.

However, there has not yet been devised and demonstrated a single sensing element which is capable of sensing both the humidity and the gas content in the surrounding atmosphere with a reliable degree of accuracy. The reason why it had been difficult to develop such multi-functional sensors becomes apparent when one considers the use of a multi-functional sensor in an automatic control system for cooking equipment such as microwave ovens. The sensing element would be exposed not only to the water vapor but also the air containing various gases and oils. Some sensing elements would undergo chemical reactions with the gases and, or oils in the air, and the gases and oils would adhere to the surfaces of the sensing element, so that sensitivity would be degraded considerably. Another reason is that the sensing elements which have been used in practice and are made of n-type tin or iron oxides cannot detect both the humidity and the gas content in the surrounding atmosphere with a satisfactory degree of accuracy.

SUMMARY OF THE INVENTION

In view of the above, the primary object of the present invention is to provide a multi-functional sensor which is capable of detecting both the water vapor and gases in the surrounding atmosphere and whose sensitivity and characteristics will not be degraded and which is highly accurate and reliable in operation.

A multi-functional sensor in accordance with the present invention has a sensing element made of a p-type metal-oxide ceramic semiconductor. In general, both the p-type and n-type semiconductors decrease their electrical resistance when they absorb water. When the n-type semiconductors absorb the reducing gases, their resistance drops, but when the p-type semiconductors absorb the reducing gases, their resistance increases. In other words, the n-type semiconductor sensing elements change their electrical resistance in inverse proportion to their absorption of both water vapor and reducing gases, so that they cannot distinguish between water vapor and reducing gases. On the other hand, the changes in resistance of the p-type semiconductor sensing elements are inversely proportional to their absorption of water but are proportional to their absorption of reducing gases. Thus they can distinguish between water vapor and reducing gases in the surrounding atmosphere. It follows, therefore, that the multi-functional sensing elements are made of p-type semiconductors.

A multi-functional sensor in accordance with the present invention uses, therefore, a sensing element made of a p-type metal-oxide ceramic semiconductor and is capable of sensing the water vapor in the surrounding atmosphere in terms of variations in the ion conduction due to the physical absorption of water vapor by the sensing element when the temperature of the sensing element and the ambient temperature are lower than 150° C. and also capable of sensing the presence of reducing gases in terms of variations in electron conduction due to the chemical absorption of reducing gases by the sensing element when the temperature of the sensing element and the ambient temperature are at temperatures between 200° and 600° C. In other words, the sensing element in accordance with the present invention can sense or detect the presence of water vapor and reducing gases depending upon the temperature of the sensing element and the ambient temperature. More specifically, the multi-functional sensor in accordance with the present invention can detect not only the relative humidity from 0 to 100% but also the concentrations of alcohols and smoke at high temperatures between 200° and 600° C. In addition, the multi-functional sensor can operate in a highly reliable and dependable manner for a long period. Thus, the multi-functional sensors in accordance with the present invention will find wide applications in various fields such as the control systems for cooking equipment.

More particularly, a sensing element made of a p-type metal-oxide ceramic semiconductor in accordance with the present invention responds at temperatures lower than 150° C. by the physical absorption and desorption of water vapor through pores of the ceramic structure. When it absorbs the water vapor, its electrical resistance drops. The reason is that when the sensing element absorbs the water vapor physically, its surfaces become a sort of electrolyte so that proton ion conduction is facilitated. Variations in electric conductance are characterized by the fact that the electrical resistance of the sensing element drops with increase in the relative humidity.

When the sensing element is heated and maintained at high temperatures above 200° C., it becomes chemically active. When the sensing element is placed in an atmosphere containing reducing gases such as hydrocarbon gases, hydrogen gas, hydrogen sulfide gas, alcohol gases and like, the chemical absorption occurs on the surfaces of the sensing element and consequently its electrical resistance increases with increase in the reducing gas content in the surrounding atmosphere. However, when the sensing element chemically absorbs oxidizing gases, its electrical resistance drops. It is the electrical resistance change that is used for detecting the reducing gas content in the surrounding atmosphere.

According to the extensive studies and experiments conducted by the inventors, it was found out that the physical absorption of water vapor by the sensing element will not occur when the temperature is higher than 200° C. Thus the sensing element in accordance with the present invention can detect the humidity and the reducing gases in the surrounding atmosphere by selecting the temperature of the sensing element itself or the ambient temperature. It was also found out that even when the surfaces of the sensing element are contaminated with oils or the like, the sensing element can be completely decontaminated by heating it to temperatures higher than 450° C. In addition, the sensing element is fabricated by sintering at high temperatures above 900° C. as will be described in detail below. It exhibits stable characteristics which are not be degraded or changed even when subjected to the decontamination process at high temperatures as described above. Thus the sensing element has a high degree of reproducibility in characteristics.

As described previously, the multi-functional sensor in accordance with the present invention can detect the humidity and the presence of reducing gases in the surrounding atmosphere depending upon the temperature of the sensing element or its ambient temperature. In other words, the multi-functional sensor in accordance with the present invention has the characteristic of the p-type semiconductor in that the electrical resistance decreases with increase in relative humidity, but increases with increase in the reducing gas content in the surrounding atmosphere. Thus the multi-functional sensor can detect both the humidity and the reducing gases in the surrounding atmosphere at the above-specified temperature ranges, respectively.

As described elsewhere, the electrical resistance of the sensing element decreases with increase in oxygen content in the surrounding atmosphere. In general, the multi-functional sensors in accordance with the present invention are used in the air which contains a large amount, about 20%, of oxygen. Thus the oxygen in the air will not adversely affect the measurements of humidity and gas contents or concentrations.

DESCRIPTION OF THE PREFERRED EMBODIMENTS

The present invention will be described in detail with reference to its preferred embodiments, but it is to be understood that the present invention is not limited thereto.

Figure 1:
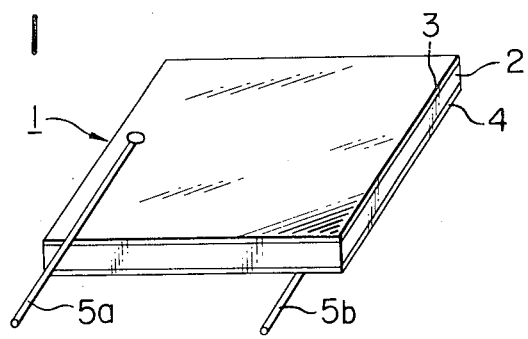
FIG. 1 is a perspective view of a sensing element in accordance with the present invention.

FIG. 1 shows a multi-functional sensing element 1 in accordance with the present invention. The sensing element 1 comprises a substrate 2 of a p-type metal-oxide ceramic semiconductor, electrode layers 3 and 4 of, for instance, $RuO_2$ formed on both the major surfaces of the substrate 2 and lead wires 5a and 5b extended from the electrodes 3 and 4, respectively.

Figure 2:
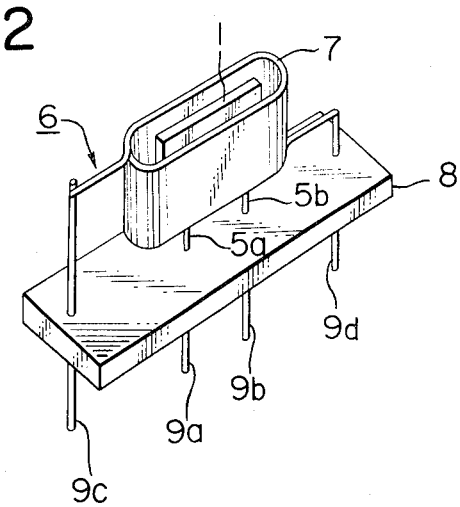
FIG. 2 is a perspective view of a multi-functional sensor incorporating the sensing element shown in FIG. 1.

The sensing element 1 is mounted on a base 8 as shown in FIG. 2. The base 8 is made of a heat resisting and electrically insulating material or medium. The sensing element 1 is surrounded by a resistance heating element 7 connected via lead wires 9c and 9d to a power supply (not shown), so that the sensing element 1 is heated by the heating element 7. The sensing element 1 is connected to a power supply (not shown) via lead wires 9a and 9b extended through the base 8. Thus a multi-functional sensor 6 is provided.

When the ambient temperature is lower than 150° C., the substrate 2 exhibits resistance the value of which depends on the humidity of the surrounding atmosphere, but when the ambient temperature rises to the region from 200° to 600° C., the substrate 2 exhibits resistance the value of which corresponds to the concentration of a gas in the surrounding atmosphere. The change in resistance of the substrate 2 can be measured between the leads 9a and 9b. The temperature of the substrate 2 itself as well as the temperature of the air surrounding the substrate 2 can be controlled by flowing the current via lead wires 9c and 9d to the heating element 7.

Figure 3:
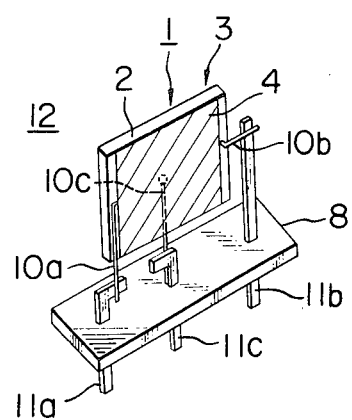
FIG. 3 is a perspective view of another embodiment of a multi-functional sensor in accordance with the present invention.

FIG. 3 shows another construction of a multi-functional sensor in accordance with the present invention. In this embodiment, one of the electrodes is used as a resistance heating element so as to directly heat the substrate 2. More particularly, the electrode 4 is used as a heating element and is connected to lead wires 10a and 10b at its opposing edges. The electrode 3 is connected to a lead wire 10c. These lead wires 10a, 10b and 10c in turn are connected to terminals 11a, 11b and 11c, respectively, which in turn are mounted on the base 8 which is made of a heat resisting and electrically insulating material. Thus a multi-functional sensor 12 is provided.

The resistance of the substrate 2 which changes depending upon the humidity in the surrounding atmosphere and the concentration of a gas in the surrounding atmosphere can be detected between the terminal 11c and either of the lead terminals 11a and 11b. The temperature of the substrate 2 itself and the temperature of the air surrounding it can be controlled and maintained at a desired level by controlling the current supplied via the terminals 11a and 11b to the electrode 4 which functions as the heating element.

Most preferably the substrate 2 is made of at least one material selected from a spinel group consisting of $MgCr_2O_4$, $FeCr_2O_4$, $NiCr_2O_4$, $MnCr_2O_4$, $CuCr_2O_4$, $CoCr_2O_4$ and $ZnCr_2O_4$. Alternatively, the substrate 2 is made of compounds whose major components are the spinels described above. In addition, the substrate 2 can be made of a p-type metal-oxide ceramic semiconductor whose major component is expressed by $(1-x)MgCr_2O_4-xTiO_2$ (where $x \leq 0.95$).

The preparation of the above-described spinels will be described below in conjunction with $MgCr_2O_4$. First finely divided MgO and $Cr_2$ are wet mixed at the ratio of 1:1 in molecular concentration. After drying, the mixture is molded into pellets of, for instance, 4 mm×4 mm×0.25 mm in size. The pellets are sintered at temperatures between 900° and 1600° C., for instance at 1300° C., so that $MgCr_2O_4$ pellets or ceramic bodies can be obtained. Other spinels can be also prepared in a manner substantially similar to that described above.

Figure 4:
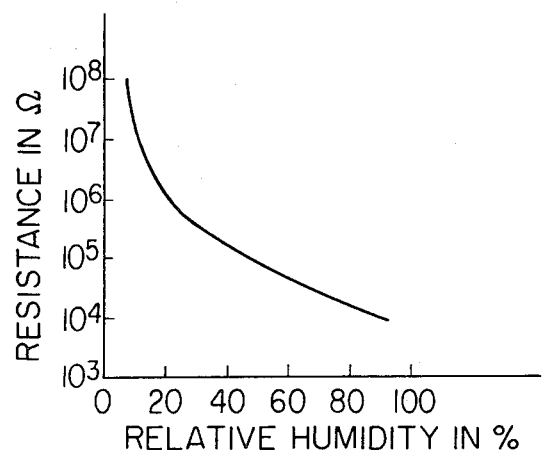
FIG. 4 shows the relationship between the relative humidity and electrical resistance of a multi-functional sensor in accordance with the present invention.

Next referring to FIGS. 4 and 5, the characteristics of the multi-functional sensors in accordance with the present invention will be described below in conjunction with a $MgCr_2O_4$ sensing element. FIG. 4 shows the relationship between the humidity and the resistance across the sensing element under no-heating condition; that is, at room temperature. It is readily seen that the resistance decreases with increase in humidity. The temperature range in which the humidity can be measured with a satisfactory degree of accuracy is below 150° C.

At temperatures lower than 150° C., the proton ion conduction is increased in the sensing element because of the physical absorption of water so that the resistance of the sensing element decreases. However, when the ambient temperature exceeds 150° C., water absorption becomes less so that the sensitivity to the humidity in terms of variation in electrical resistance drops remarkably.

When the sensing element is placed in the atmosphere at a temperature lower than 150° C. and is not heated, the resistance hardly changes even when the surrounding atmosphere contains reducing gases such as carbon monoxide, isobutane, ethyl alcohol, hydrogen and so on.

Figure 5:
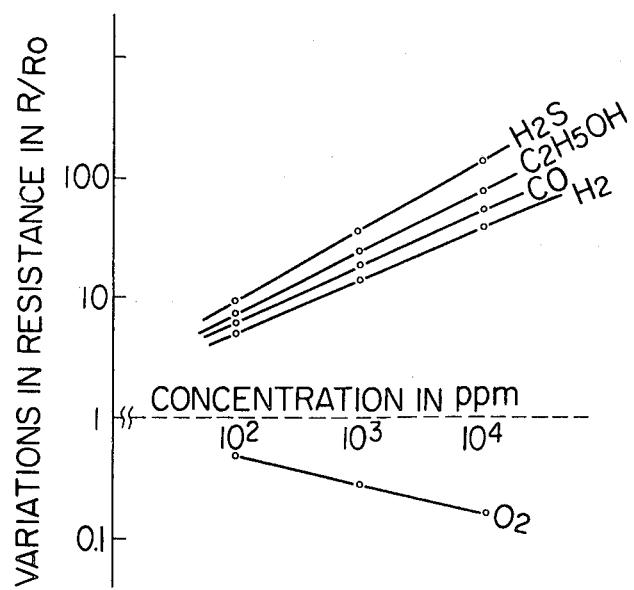
FIG. 5 shows sensitivity of the same sensor to reducing gases in the air.

FIG. 5 shows the relationship between the resistance across the sensing element and the content, in ppm, of a reducing gas in the surrounding atmosphere when the heating element is energized so as to maintain the temperature of the sensing element at 400° C. In FIG. 5, $R_o$ indicates the resistance of the sensing element when placed in an inert gas atmosphere and R shows the resistance when the sensing element is placed in the atmosphere of $H_2S$, $C_2H_5OH$, CO or $H_2$ and the concentration of the reducing gas is varied.

From FIG. 5 it is seen that the higher the concentration of the reducing gas, the higher the resistance of the sensing element becomes. When the sensing element is removed from a reducing gas atmosphere and placed in an inert gas atmosphere, the sensing element shows its initial resistance. The sensitivity of the sensing element is high when the ambient temperature around the sensing element is maintained between 200° C. and 600° C. In addition, the concentration-resistance characteristic curves exhibit no hysteresis.

The sensing elements made of other compounds than $MgCr_2O_4$ show the humidity-resistance characteristics and the gas content-resistance characteristics substantially similar to those described above in conjunction with a typical example of $MgCr_2O_4$. The results of the experiments conducted by the inventors are shown in TABLE 1.

alcohol of 100 and 1000 ppm and was maintained at 450° C. is expressed in terms of the ratio $R/R_o$. The sensing elements in accordance with the present invention exhibited similar gas sensitivity at the presence of other reducing gases such as hydrocarbon gases, hydrogen gas, hydrogen sulfide gas, alcohol gas and so on.

As shown in TABLE 1, the value x of $(1-x)$ $MgCr_2O_4$—$xTiO_2$ sensing elements were varied from 0 to 0.99. It is seen that regardless of the value x, the sensing elements exhibited satisfactory sensitivity to both humidity and reducing gases, but when the value x exceeds 0.95, sensitivity to humidity and reducing gases drops and, furthermore, resistance to thermal spalling decreases. It follows, therefore, that the value x preferably is between 0 and 0.95 in practice.

Sensitivity to humidity and reducing gases can be improved when the above-described p-type metal-oxide ceramic semiconductor compounds are modified by the addition of one or more compounds selected from the oxides such as NiO, MgO, $Fe_2O_3$, $ZrO_2$, $Al_2O_3$, $Ir_2O_3$, $Cr_2O_3$, $SiO_2$, CoO, CuO, $HfO_2$, $MnO_2$ and so on, and spinels, perovskites, tungsten bronze, pyrochlore and so on.

As compared with the sensor of the type shown in FIG. 2, the sensor of the type in which one of the electrodes is used as a heating element as shown in FIG. 3 is advantageous because the power consumption (for heating the sensing element 1) can be lowered and the thermal response can be improved. It should be noted, however, that both types have satisfactory sensitivity to humidity and reducing gases.

Figure 6:
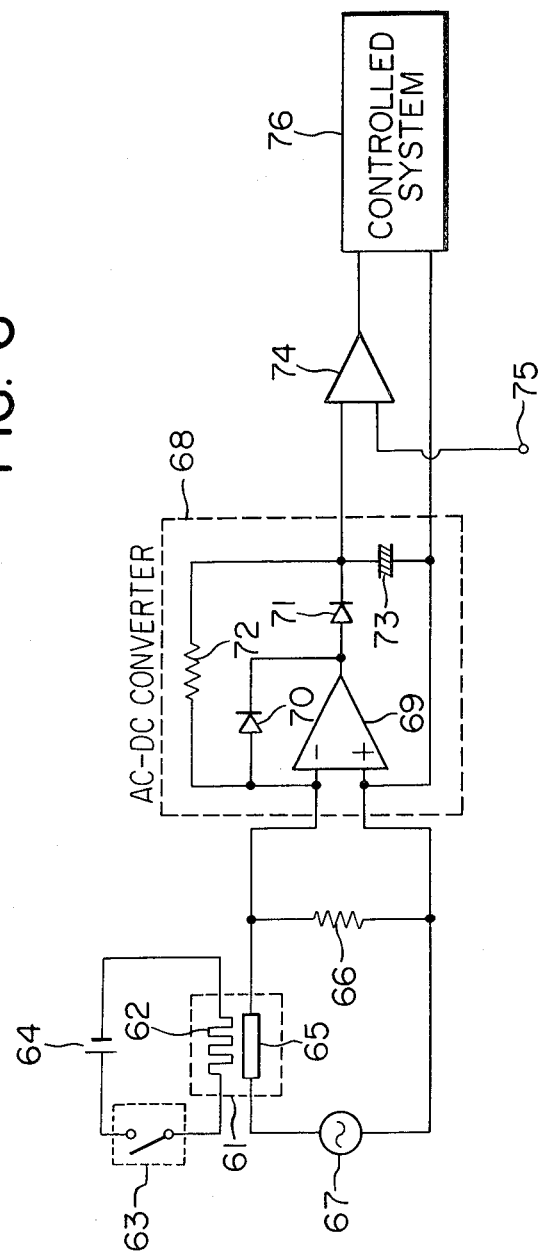
FIG. 6 is a circuit diagram of a device incorporating a multi-functional sensor in accordance with the present invention in order to control a system in response to the output of the sensor.

FIG. 6 is a circuit diagram of a device incorporating the multi-functional sensor in accordance with the present invention. The sensor generally indicated by 61 has a heating element 62 connected in series with a switch 63 to a DC power supply 64. When the switch 63 is turned off, a sensing element 65 of the sensor 61 can be maintained at temperatures lower than 150° C. When the switch 63 is turned on to energize the heating element 62, the sensing element 65 is maintained at temperatures between 200° C. and 600° C.

The sensing element 65 and a resistor 66 are connected in series to an AC power supply 67 of, for instance, 1 V and 70 Hz. The voltage and frequency of the

TABLE 1

| Specimen Nos. | Composition | Sensitivity to humidity ($\Omega$) at 20° C. | | Sensitivity to gas, i.e., ethyl alcohol gas at 450° C. | |
|---|---|---|---|---|---|
| | | 20% RH | 80% RH | 100 ppm (R/Ro) | 1000 ppm (R/Ro) |
| 1 | $FeCr_2O_4$ | $1.2 \times 10^6$ | $1.0 \times 10^4$ | 7.5 | 22.5 |
| 2 | $NiCr_2O_4$ | $1.6 \times 10^6$ | $1.1 \times 10^4$ | 7.0 | 21.0 |
| 3 | $MnCr_2O_4$ | $3.1 \times 10^6$ | $1.6 \times 10^4$ | 8.2 | 24.6 |
| 4 | $CuCr_2O_4$ | $1.0 \times 10^6$ | $9.5 \times 10^3$ | 8.6 | 25.8 |
| 5 | $CoCr_2O_4$ | $1.2 \times 10^6$ | $1.2 \times 10^4$ | 7.4 | 22.2 |
| 6 | $ZnCr_2O_4$ | $1.2 \times 10^6$ | $1.1 \times 10^4$ | 8.8 | 26.4 |
| 7 | $Cr_2O_3$ | $3.4 \times 10^6$ | $2.3 \times 10^4$ | 8.0 | 24.0 |
| 8 | 1.0 $MgCr_2O_4$—0.0 $TiO_2$ | $1.5 \times 10^6$ | $1.5 \times 10^4$ | 9.8 | 28.2 |
| 9 | 0.99 $MgCr_2O_4$—0.001 $TiO_2$ | $3.0 \times 10^6$ | $1.6 \times 10^4$ | 12.0 | 36.0 |
| 10 | 0.90 $MgCr_2O_4$—0.10 $TiO_2$ | $2.0 \times 10^6$ | $1.5 \times 10^4$ | 12.4 | 37.2 |
| 11 | 0.80 $MgCr_2O_4$—0.20 $TiO_2$ | $1.5 \times 10^6$ | $1.6 \times 10^4$ | 12.6 | 35.4 |
| 12 | 0.60 $MgCr_2O_4$—0.40 $TiO_2$ | $1.5 \times 10^6$ | $2.0 \times 10^4$ | 12.5 | 39.5 |
| 13 | 0.40 $MgCr_2O_4$—0.60 $TiO_2$ | $1.3 \times 10^6$ | $4.0 \times 10^4$ | 13.0 | 44.1 |
| 14 | 0.20 $MgCr_2O_4$—0.80 $TiO_2$ | $8.0 \times 10^5$ | $5.0 \times 10^4$ | 12.8 | 44.3 |
| 15 | 0.05 $MgCr_2O_4$—0.95 $TiO_2$ | $6.0 \times 10^5$ | $7.0 \times 10^4$ | 12.0 | 43.2 |
| 16 | 0.001 $MgCr_2O_4$—0.99 $TiO_2$ | $8.0 \times 10^5$ | $7.0 \times 10^4$ | 3.0 | 9.0 |

In TABLE 1, sensitivity is expressed in terms of electrical resistance when the sensing element was placed in the atmosphere at 20° C. and 20 or 80% RH (relative humidity). Sensitivity to the reducing gases when the sensing element was placed in an atmosphere of ethyl AC power supply 67 are not limited to the above-described values and may be suitably selected depending upon the use of the device.

An AC-DC converter generally indicated by the reference numeral 68 comprises an operational amplifier 69 whose input is a voltage across the resistor 66, diodes 70 and 71, a resistor 72 and a capacitor 73. The AC-DC converter 68 converts the AC voltage across the resistor 66 into a DC voltage which in turn is applied to a comparator 74. The comparator 74 compares the DC voltage output from the AC-DC converter 68 with a reference voltage applied at a terminal 75 and delivers to a controlled system 76 the signal representative of the difference between the input voltage and the reference voltage. Both the operational amplifier 69 and the comparator 74 may be of the conventional types.

When the switch 63 is kept turned off, the sensor 61 responds to the water vapor in the surrounding atmosphere. More specifically, the sensing element 65 changes its resistance in response to variations in humidity of the surrounding atmosphere as described elsewhere. When the relative humidity rises, the resistance of the sensing element 65 drops so that the voltage across the output resistor 66 rises. The voltage across the resistor 66 is then converted into a DC voltage by the AC-DC converter 68 and applied to the comparator 74 for comparison with the reference voltage impressed at the terminal 75, the reference voltage representing a desired humidity. In response to the output from the comparator 74, the system 76 is controlled.

When the switch 63 is turned on, the sensor 61 responds to the reducing gases in the surrounding atmosphere. More specifically, the heating element 62 is energized so that the sensing element 65 is maintained at, for instance, 400° C. As described previously, the resistance of the sensing element 65 increases with increase in the concentration of the reducing gas in the surrounding atmosphere. This time the output from the AC-DC converter 68, which represents the concentration of the reducing gas in the surrounding atmosphere, is compared with a reference voltage representative of a given level of concentration. In response to the output from the comparator 74 the system 76 is controlled.

When the system 76 to be controlled is an air conditioner, its humidifying device or de-humidifying device is activated in response to the output from the comparator 74 when the relative humidity in a room drops below or rises above a preset level. When the device shown in FIG. 6 detects the concentration above a toxic level of reducing gases in the air in the room, the air conditioner can generate a warning or alarming signal or activate its exhaust fan so as to exhaust the air contaminated with the reducing gases to the exterior, thereby dropping the concentration of toxic gases below a safe level.

When the system 76 to be controlled is a cooking equipment comprising a microwave oven and an electric oven, the microwave oven can be controlled in response to the output from the comparator 74 representative of the humidity and the electric oven can be controlled in response to the output representing the concentration of gases in the oven. Alternatively, the microwave oven can be controlled in response to the output representative of the concentration of gases in the oven while the electric oven can be controlled in response to the output representative of the humidity in the oven. Furthermore, the microwave or electric oven can be controlled in response to both the output representative of the humidity and the concentration of gases which are alternately measured.

In summary, according to the present invention, the multi-functional sensor can separately detect the humidity and the concentration of reducing gases in the surrounding atmosphere and is adapted to the mass production.

What is claimed is:

1. A multi-functional sensor capable of detecting humidity and a gas or gases comprising
   (a) a sensing element consisting essentially of a p-type metal-oxide ceramic semiconductor,
   (b) means attached to said sensing element for detecting or measuring humidity in terms of variations in ion conduction due to the physical absorption of water, temperature lower than 150° C., and
   (c) means attached to said sensing element for detecting or measuring a gas or gases in terms of variations in electron conduction due to the chemical absorption of said gas or gases at temperature between 200° C. and 600° C.

2. A multi-functional sensor as set forth in claim 1 further comprising
   a heating means for heating said single sensing element at temperatures between 200° C. and 600° C.

3. A multi-functional sensor as set forth in claim 2 wherein
   said heating means is disposed adjacent to said single sensing element.

4. A multi-functional sensor as set forth in claim 2 wherein
   said heating means is formed integral with said single sensing element.

5. A multi-functional sensor as set forth in claim 1 wherein
   the major component of said p-type metal-oxide ceramic semiconductor consists of at least one compound selected from the group consisting of $MgCr_2O_4$, $FeCr_2O_4$, $NiCr_2O_4$, $MnCr_2O_4$, $CuCr_2O_4$, $CoCr_2O_4$ and $ZnCr_2O_4$.

6. A multi-functional sensor as set forth in claim 1 wherein
   said p-type metal-oxide ceramic semiconductor is made of a compound expressed by $(1-x)MgCr_2O_4 - xTiO_2$, where $0 < x < 0.95$.

* * * * *